(12) United States Patent
Biggs et al.

(10) Patent No.: US 6,339,137 B1
(45) Date of Patent: Jan. 15, 2002

(54) POLY(AMINOORGANOFUNCTIONALSILOXANES)

(75) Inventors: Timothy N. Biggs, Gainesville, FL (US); Benigno A. Janeiro, Burlington, NJ (US)

(73) Assignee: Archimica (Florida) Inc., Gainesville, FL (US)

(*) Notice: Subject to any disclaimer, the term of this patent is extended or adjusted under 35 U.S.C. 154(b) by 0 days.

(21) Appl. No.: 09/532,714

(22) Filed: Mar. 22, 2000

(51) Int. Cl.$^7$ .................. C08G 77/08; C08G 77/26
(52) U.S. Cl. .................. 528/14; 528/12; 528/21; 528/23; 528/33; 528/37; 528/38; 556/413; 556/425; 556/466; 556/467
(58) Field of Search .................. 528/12, 14, 21, 528/23, 33, 37, 38; 556/413, 425, 466, 467

(56) References Cited

U.S. PATENT DOCUMENTS

| | | | |
|---|---|---|---|
| 2,947,771 A | * 8/1960 | Bailey | |
| 3,045,036 A | * 7/1962 | Jex et al. | |
| 3,775,452 A | 11/1973 | Karstedt et al. | 260/429 |
| 3,814,730 A | 6/1974 | Karstedt et al. | 260/46.5 |
| 4,680,366 A | * 7/1987 | Tanaka et al. | 528/27 |
| 4,736,049 A | 4/1988 | Suzuki et al. | 556/479 |
| 4,897,501 A | * 1/1990 | Takatsuna et al. | 556/413 |
| 4,921,988 A | * 5/1990 | Takatsuna et al. | 556/413 |
| 4,927,953 A | * 5/1990 | Takatsuna et al. | 556/413 |
| 5,026,890 A | 6/1991 | Webb et al. | 556/408 |
| 5,391,675 A | 2/1995 | Cray et al. | 528/14 |
| 5,486,634 A | 1/1996 | Hahn et al. | 556/425 |
| 5,892,084 A | 4/1999 | Janeiro et al. | 556/425 |

FOREIGN PATENT DOCUMENTS

| | | | |
|---|---|---|---|
| DE | 2408480 | 9/1975 | C07F/7/18 |
| EP | 0321174 | 6/1989 | C07F/7/08 |
| GB | 2185984 | 8/1987 | C07F/7/10 |
| JP | 11209384 | 8/1999 | |

* cited by examiner

*Primary Examiner*—Robert Dawson
*Assistant Examiner*—Jeffrey B. Robertson
(74) *Attorney, Agent, or Firm*—Hedman & Costigan, P.C.

(57) ABSTRACT

The present invention provides near quantitative yields of greater than about 95% isomeric purity of poly(3-aminopropylmethylsiloxanes) of the general formulae:

$$Me_3Si(H_2NCH_2CH_2CH_2MeSiO)_xOSiMe_3$$

$$(H_2NCH_2CH_2CH_2MeSiO)_y$$

wherein Me is methyl, x may range from 2 to about 100 and y may range from 3 to about 7. The present invention also provides a simple method for rapidly producing poly(3-aminopropylmethylsiloxanes) of the general formulae:

$$Me_3Si(H_2NCH_2CH_2CH_2MeSiO)_xOSiMe_3$$

$$(H_2NCH_2CH_2CH_2MeSiO)_y$$

wherein Me is methyl, x may range from 2 to over 100 and y may range from 3 to about 7, the method comprising heating of 3-(3-aminopropyl)-1,1,1,3,5,5,5-heptamethyltrisiloxane, of at least 95% isomeric purity, with a basic catalyst, removing hexamethyldisiloxane, and decomposing the catalyst.

14 Claims, No Drawings

POLY (AMINOORGANOFUNCTIONALSILOXANES)

FIELD OF THE INVENTION

The present invention relates to high purity poly(3-aminopropylmethylsiloxanes) and a method for their preparation. More specifically, the present invention relates to more than 95% isomerically pure poly(3-aminopropylmethylsiloxane) fluids, both linear and cyclic, prepared by the base catalyzed detrimethylsilylation and polymerization of at least 95% isomerically pure 3-(3-aminopropyl)-1,1,1,3,5,5,5-heptamethyltrisiloxane. These poly(3-aminopropylmethylsiloxanes) have utility as intermediates for other derivative poly (organofunctionalsiloxanes) and in cosmetic, textile, and automotive applications, and as coatings and adhesives.

BACKGROUND OF THE PRESENT INVENTION

There is considerable prior art relating to the synthesis of poly(aminoalkylmethylsiloxanes). Generally, poly (aminoalkylmethylsiloxanes) have been produced by first preparing aminoalkylmethyldialkoxysilanes, followed by hydrolysis with or without an endblocking agent, such as a trimethylsilyl derivative, to form cyclic and linear poly(3-aminoalkylmethylsiloxanes). The isomeric purity of the poly (aminoalkylmethylsiloxane) fluids, prepared in the manner of the prior art, is dependent upon the isomeric purity of the aminoalkylmethyldialkoxysilane prepared in the first step of the synthesis. German Patent No. 2408480 describes the reaction of a silazane derivative from allylamine and an organohydrochlorosilane, in the presence of a proton acceptor to form an intermediate silazane which then undergoes a hydrosilylation reaction catalyzed by a platinum catalyst. Upon alcoholysis, the intermediate hydrosilylation product forms 3-aminopropylmethyldiethoxysilane in 70% overall yield. A molar excess of at least 50% of allylamine is used in this process. Identification of the beta-isomer in the product was not made. Japanese Patent No. 10017578 describes another method of synthesis by hydrosilylation of N,N-bis(trimethylsilyl)allylamine by methyldimethoxysilane. The product of that reaction is then heated with methanol to form 3-aminopropylmethyldimethoxysilane in at least 85% overall yield. The presence of the beta-isomer in the product was not made. Japanese Patent No. 11209384 describes the use of a rhodium:cyclooctadiene complex as a hydrosilylation catalyst for the addition of methyldiethoxysilane to allylamine to form 3-aminopropylmethyldiethoxysilane in 78% yield. 2-Aminopropylmethyldiethoxysilane is formed at very low levels in this process not exceeding 0.5%. U.S. Pat. No. 5,391,675 describes the formation of an aminopropylmethylsiloxy-containing polydimethylsiloxane by barium or strontium hydroxide catalyzed condensation of a silanol terminated polydimethylsiloxane with a 3-aminopropylalkoxysilane with elimination of an alcohol.

However, none of the prior art references disclose the high isomeric purity poly(3-aminopropylmethylsiloxanes) of the present invention. The poly(3-aminopropylmethylsiloxanes) of the present invention have improved utility as intermediates for producing other poly(organofunctionalsiloxanes), and in cosmetic, textile and automotive applications, and as coatings and adhesives.

SUMMARY OF THE INVENTION

The present invention provides near quantitative yields of greater than about 95% isomeric purity of poly(3-aminopropylmethylsiloxanes) of the general formulae

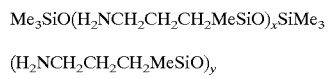

$$Me_3SiO(H_2NCH_2CH_2CH_2MeSiO)_xSiMe_3$$

$$(H_2NCH_2CH_2CH_2MeSiO)_y$$

wherein Me is methyl, x may range from 2 to about 100 or more and y may range from 3 to about 7.

The present invention also provides a simple method for rapidly producing poly(3-aminopropylmethylsiloxanes) of the general formulae:

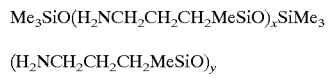

$$Me_3SiO(H_2NCH_2CH_2CH_2MeSiO)_xSiMe_3$$

$$(H_2NCH_2CH_2CH_2MeSiO)_y$$

wherein Me is methyl, x may range from 2 to about 100 or more and y may range from 3 to about 7, the method comprising heating of 3-(3-aminopropyl)-1,1,1,3,5,5,5-heptamethyltrisiloxane, of at least 95% isomeric purity, with a basic catalyst, and removing hexamethyldisiloxane.

DETAILED DESCRIPTION OF THE PRESENT INVENTION

The present invention provides near quantitative yields of greater than about 95% isomeric purity of poly(3-aminopropylmethylsiloxanes) of the general formulae:

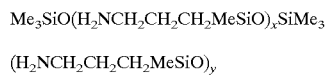

$$Me_3SiO(H_2NCH_2CH_2CH_2MeSiO)_xSiMe_3$$

$$(H_2NCH_2CH_2CH_2MeSiO)_y$$

wherein Me is methyl, x may range from 2 to about 100 or more and y may range from 3 to about 7. The present invention also provides high purity poly(3-aminopropylmethylsiloxane) homopolymers which are greater than about 97% free of hexamethyldisiloxane and are substantially free of other organic and inorganic compounds. The ratio of linear to cyclic polymers in the fluids of the present invention can vary widely but are typically in the range of from about 1:10 to about 10:1.

The present invention also provides a novel method for producing the high isomeric purity poly(3-aminopropylmethylsiloxanes) of the present invention, the process comprising (a) mixing 3-(3-aminopropyl) heptamethyltrisiloxane with a basic catalyst, (b) heating the mixture to produce the homopolymers of the present invention and hexamethyldisiloxane and volatilizing the hexamethyldisiloxane out of the mixture, (c) evacuating the mixture to remove residual hexamethyldisiloxane, and (d) heating the evacuated product to thermally decompose the basic catalyst and recovering the high isomeric purity poly (3-aminopropylmethylsiloxane) homopolymer product.

Preferably the 3-(3-aminopropyl)heptamethyltrisiloxane is 3-(3-aminopropyl)-1,1,1,3,5,5,5-heptamethyltrisiloxane of at least 95% isomeric purity, which is preferably prepared according to the instructions set forth in U.S. Pat. No. 5,892,084.

The basic catalysts useful in the practice of the present invention include most metal hydroxides, metal oxides, quaternary organoammonium hydroxides, quaternary organo-phosphonium hydroxides, and metal trimethylsilanolates. The preferred catalysts are quaternary organoammonium hydroxides, quaternary organophosphonium hydroxides, and metal trimethyl-silanolates. A particularly useful catalyst for the detrimethylsilylation and polymerization of the present invention is tetramethylammonium hydroxide. The catalyst is typically employed in a concentration ranging from about 100 ppm to about 10,000 ppm, preferably from about 1,000 ppm to about 5,000 ppm, and most preferably from about 2,000 to about 4,000 ppm, based on the weight of the 3-(3-aminopropyl)heptamethyltrisiloxane.

The polymerization step (b), which proceeds by elimination of hexamethyldisiloxane from 3-(3-aminopropyl)-1,1,1,3,5,5,5-heptamethyltrisiloxane, of at least 95% isomeric purity, can be carried out at temperatures ranging from about 80° C. to about 200° C., preferably from about 80° C. to about 150° C., and more preferably between about 100° C. and about 130° C. Preferably the heating of the mixture should continue until no further hexamethyldisiloxane is observed to be volatilizing from the residual mixture.

The product of the polymerization/volatilization step (b) is then subjected to evacuation to remove dissolved residual hexamethyldisiloxane. This step is effected by reducing the pressure of the polymerized product to a pressure of about 200 mm Hg, or other pressures as will be apparent to those of ordinary skill in the art.

The evacuated mixture comprising the homopolymers of the present invention and the catalyst are then heated to a temperature in the range of from about 130° C. to about 160° C. for at least about 2 hours in order to decompose the catalyst, and to drive off the catalyst decomposition products. In this manner, homopolymers of the present invention are formed which are at least about 97% free of hexamethyldisiloxane and which are substantially free, i.e., 98% or more, of other organic and inorganic compounds.

The present invention also contemplates the vacuum distillation of the homopolymers of the present invention in order to isolate the individual homopolymer components or mixtures thereof, such as to isolate the cyclic polymers, including the isolation of $(H_2NCH_2CH_2CH_2MeSiO)_3$.

DESCRIPTION OF THE PREFERRED EMBODIMENTS

The following examples illustrate the present invention. They are not construed to limit the scope of the appended claims in any manner whatsoever.

EXAMPLE 1

To a 500 ml round bottom flask equipped with a stirrer, condenser, thermometer, strip head, heating mantle and nitrogen overgas was added 338 g (1.2 mole) of at least 95% isomerically pure 3(3-aminopropyl) heptamethyltrisiloxane (prepared in accordance with the teachings of U.S. Pat. No. 5,892,084) and 1 g (3000 ppm) of tetramethylammonium hydroxide. This mixture was heated to 80° C. in 30 minutes. The temperature of the mixture was then elevated to 130° C., during which time 108 g (0.67 mole) of hexamethyldisiloxane distilled over the range of 105–115° C. (755 mm of Hg pressure). Remaining in the flask was 222 g of at least 95% isomerically pure poly(3-aminopropylmethylsiloxane) which based upon amine equivalency analysis had a degree of polymerization of 2.25 and an average molecular weight of 411.

EXAMPLE 2

To a 500 ml round bottom flask equipped with a stirrer, condenser, thermometer, strip head, heating mantle and nitrogen overgas was added 324 g (1.16 mole) of at least 95% isomerically pure 3(3-aminopropyl) heptamethyltrisiloxane (prepared in accordance with the teachings of U.S. Pat. No. 5,892,084) and 1 g (3000 ppm) of tetramethylammonium hydroxide. This mixture was heated. The temperature of the mixture was then elevated to 194° C., during which time 113 g (0.70 mole) of hexamethyldisiloxane distilled over the range of 105–115° C. (755 mm of Hg pressure). Remaining in the flask was 213 g of product. At this point 48 g of this product was removed as a retain. The flask was then cooled to 50° C. and evacuated to 200 mm of Hg pressure. While heating to 90° C., 44 g (0.27 mole) of hexamethyldisiloxane was strip distilled. Based upon amine equivalency analysis, the at least 95% isomerically pure poly(3-aminopropylmethylsiloxane) product had a degree of polymerization of 9.1 and an average molecular weight of 1227. Gel permeation chromatography indicated that the product was 36% cyclosiloxanes and 64% linear poly(3-aminopropylmethylsiloxane). Assuming the average cyclosiloxane has a degree of polymerization of 5, the average molecular weight of the linear fraction is approximately 1585 with a degree of polymerization of 14.

Gas layer chromatography of the above product showed the presence of several lower molecular weight oligomeric compounds. The above product was vacuum distilled to isolate several individual components, one of which was tris(3-aminopropylmethyl)cyclotrisiloxane, which was further identified by Mass Spectrometric analysis. This compound showed a cracking pattern typical of that of a primary amine (P-30) in combination with that which is typical of all methyl substituted organosilicon compounds (P-15).

Variations of the present invention will suggest themselves to those skilled in the art in light of the above detailed descriptions. It should be understood that the forms of the invention described herein are exemplary only, and are not intended to be limitations on the scope of the present invention which is defined in the appended claims.

The above mentioned patents are all hereby incorporated by reference.

What is claimed is:

1. A process for the production of poly(3-aminopropylmethylsiloxane)homopolymer fluids of the general formulae:

$(H_2NCH_2CH_2CH_2MeSiO)_y$ wherein Me is methyl, x ranges from 2 to about 100, and y ranges from 3 to about 7, said fluid being of at least said process comprising the steps of:
  (a) mixing 3-(3-aminopropyl)heptamethyltrisiloxane having at least 95% isomeric purity with a basic catalyst;
  (b) heating the mixture to produce poly(3-aminopropylmethylsiloxane)homopolymer and hexamethyldisiloxane and to volatilize said hexamethyldisiloxane out of the mixture;
  (c) evacuating the mixture to remove residual hexamethyldisiloxane from said homopolymer; and
  (d) heating the product to thermally decompose the basic catalyst and recovering said poly(3-aminopropylmethylsiloxane)homopolymer product which is at least about 95% isomeric purity with respect to the position of each primary amino group in the 3 position of the propyl substituents.

2. A process as defined in claim 1 wherein said process produces said poly(3-aminopropylmethylsiloxane) homopolymer which is at least about 97% free of hexamethyldisiloxane and substantially free of organic and inorganic compounds.

3. A process as defined in claim 1 wherein the basic catalyst is selected from the group consisting of metal hydroxides, metal oxides, quaternary organoammonium hydroxides, quaternary organophosphonium hydroxides, metal trimethylsilanolates and mixtures of any of the foregoing.

4. A process as defined in claim 3 wherein the basic catalyst is selected from the group consisting of quaternary organoammonium hydroxides, quaternary organophosphonium hydroxides, metal trimethylsilanolates and mixtures of any of the foregoing.

5. A process as defined in claim 4 wherein the basic catalyst comprises tetramethylammonium hydroxide.

6. A process as defined in claim 1 wherein the concentration of basic catalyst, relative to 3-(3-aminopropyl) heptamethyltrisiloxane ranges from about 100 ppm to about 10000 ppm.

7. A process as defined in claim 1 wherein the concentration of basic catalyst, relative to 3-(3-aminopropyl) heptamethyltrisiloxane ranges from about 1000 ppm to about 5000 ppm.

8. A process as defined in claim 1 wherein the concentration of basic catalyst, relative to 3-(3-aminopropyl) heptamethyltrisiloxane ranges from about 2000 ppm to about 4000 ppm.

9. A process as defined in claim 1 wherein the mixture is heated in said step (b) to a temperature in the range of from about 80° C. to about 200° C. to volatilize hexamethyldisiloxane out of the mixture, said heating being terminated when no additional hexamethyldisiloxane is observed to be volatilizing from the residual mixture.

10. A process as defined in claim 9 wherein said mixture is heated in said step (b) to a temperature in the range of from about 100° to about 130° C.

11. A process as defined in claim 9 wherein said residual mixture is evacuated to about 200 mm Hg to remove dissolved hexamethyldisiloxane.

12. A process as defined in claim 10 wherein the evacuated mixture is heated to a temperature in the range of from about 130° C. to about 160° C. for at least about 2 hours to decompose the catalyst.

13. A process as defined in claim 1 further comprising the step of vacuum distilling the homopolymer product to isolate the individual homopolymer components.

14. A process as defined in claim 13 wherein a cyclic homopolymer of the general formula $$(H_2NCH_2CH_2CH_2MeSiO)_3$$

is isolated.

* * * * *